(12) United States Patent
Baynham

(10) Patent No.: US 9,987,059 B2
(45) Date of Patent: Jun. 5, 2018

(54) CERVICAL PLATE WITH SCREW LOCK RETENTION CLIP

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 227 days.

(21) Appl. No.: 14/214,445

(22) Filed: Mar. 14, 2014

(65) Prior Publication Data

US 2015/0257804 A1 Sep. 17, 2015
US 2017/0020588 A9 Jan. 26, 2017

Related U.S. Application Data

(60) Provisional application No. 61/801,017, filed on Mar. 15, 2013, provisional application No. 61/785,474, filed on Mar. 14, 2013.

(51) Int. Cl.
*A61B 17/80* (2006.01)
*A61B 17/70* (2006.01)

(52) U.S. Cl.
CPC ...... *A61B 17/8047* (2013.01); *A61B 17/7059* (2013.01); *A61B 17/80* (2013.01)

(58) Field of Classification Search
CPC ............ A61B 17/8042; A61B 17/8047; A61B 17/8033; A61B 17/8038
See application file for complete search history.

(56) References Cited

U.S. PATENT DOCUMENTS

| | | | | |
|---|---|---|---|---|
| 2006/0293670 | A1* | 12/2006 | Smisson, III | A61B 17/8042 606/250 |
| 2009/0187218 | A1* | 7/2009 | Schaffhausen | A61B 17/8042 606/286 |
| 2009/0234393 | A1* | 9/2009 | Sournac | A61B 17/7059 606/286 |
| 2012/0310289 | A1* | 12/2012 | Bottlang | A61B 17/8004 606/291 |

* cited by examiner

*Primary Examiner* — Julianna N Harvey
(74) *Attorney, Agent, or Firm* — McHale & Slavin, P.A.

(57) ABSTRACT

A cervical plate having improved mounting screws that employ a retention clip for automatically engaging the head portion of the screw during insertion into countersunk apertures. The arrangement prevents the mounting screws from migrating out of the bone material during use.

7 Claims, 10 Drawing Sheets

CERVICAL PLATE WITH SCREW LOCK RETENTION CLIP

PRIORITY CLAIM

In accordance with 37 C.F.R. 1.76, a claim of priority is included in an Application Data Sheet filed concurrently herewith. Accordingly, the present invention claims priority to U.S. provisional patent application Ser. No. 61/801,017, filed on Mar. 15, 2013, entitled "CERVICAL PLATE WITH RESILIENT RETENTION SCREW LOCK", and U.S. provisional patent application Ser. No. 61/785,474, filed on Mar. 14, 2013, entitled "CERVICAL PLATE WITH SCREW LOCK RETENTION CLIP" the contents of which are hereby expressly incorporated herein by reference.

FIELD OF THE INVENTION

This invention relates to the field of orthopedic surgery and, particularly, to the area of spinal implants for stabilizing the spatial relationship of vertebrae.

BACKGROUND OF THE INVENTION

The spine consists of vertebrae that are cauterized into sections known as the cervical, thoracic and lumbar section in a flexible arranged column. The vertebrae are separated by small cartilaginous cushions known as intervertebral discs. Intervertebral discs are oblate spherical structures that maintain the space between adjacent vertebrae. Each intervertebral disc consists of an outer annulus fibrosus, which surrounds the inner nucleus pulposus. The annulus fibrosus consists of several layers of strong annular fibrocartilage to contain the nucleus pulposus and distribute pressure evenly across the disc wherein a mucoprotein gel serves to absorb shocks.

Deterioration of an intervertebral disc results in limited mobility and can cause severe pain. For instance, normal aging causes the nucleus pulposus to lose fluid and contract in volume resulting in a reduction in the intervertebral space. Any reduction of space between adjacent vertebrae may put pressure on the nerves of the spinal column. Further, a reduction in volume of the nucleus pulposus reduces the disc's ability to absorb shock which can result in disc herniation. The bulge of a herniated disc may also put pressure on nearby nerve structures resulting in pain as well as diminished range of motion.

Surgical options are available including laminectomy and discectomy combined with vertebral fusion and/or dynamic stabilization. However, these surgical options are highly invasive and require prolonged hospitalization and recovery. More recently, artificial disc replacement prosthetics have been used to replace or augment all or part of the removed or resected intervertebral disc.

In order to reduce the pain associated with the movement of the intervertebral joint, surgical intervention is often indicated as a means to alleviate pressure upon the spinal cord while concomitantly stabilizing the associated vertebrae.

Spinal plates are well known in the orthopedic art for fixing bones or bone fragments in a pre-selected spatial orientation. The plates are usually attached to the bones or bone fragments by screws designed to make a secure and long lasting connection not affected by the loads caused by normal activities of the host.

SUMMARY OF THE INVENTION

Embodiments of the invention are directed, inter alia, to a cervical plate having improved mounting screws that employ retention clips which engage the plate and fit over the screw heads. The screw heads engage the retention clip during installation allowing ease of insertion wherein the mounting screws pushes aside a portion of the retention clip. If the mounting screw is not fully inserted, the retention clip will not engage the screw head providing a visual indicator of proper screw head positioning. The retention clip is constructed to automatically engage the head portion of the screws during insertion of the screw into countersunk apertures. The arrangement prevents the mounting screws from migrating out of the bone material during use.

In particular embodiments, a cervical plate having an improved mounting that employs a PEEK spring, or another material having a defined memory, is positioned in the mounting hole of a plate to maintain a mounting screw in position. The screw head engages the PEEK spring that is constructed and arranged to form a taper, wherein the screw head stretches the PEEK spring during installation and prevents the screw from reversing.

Therefore, it is an objective of this invention to provide a cervical plate having at least one screw receiver spaced along the length of the plate for accepting a screw. The retention clips are formed from a spring type material which engages the screw heads to allow the screws to be rotated inward or outward, until the screw head passes the retention clip and is locked into position.

Thus an objective of this invention is to provide a cervical plate having a locking mechanism that is operated simultaneously with the positioning of the screws in receivers along the plate.

A further objective of this invention is to provide a cervical plate having an automatic locking mechanism which engages each screw to prevent back out migration of the screws.

It is an objective of this invention to provide a cervical plate adapted to span the intervertebral space and having at least two screw receivers spaced along the length of the plate having screw receivers each have countersunk apertures for accepting the heads of mounting screws with a spring material to engage the screw head to prevent backing out of the screw.

A further objective of this invention is to provide a cervical plate having an automatic locking mechanism which engages each screw to prevent back out migration of the screws.

Still another objective of this invention is to provide a cervical plate having a spring formed from a PEEK material that can be automatically stretched during installation and removed to permit post-operative removal of the screw is necessary.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
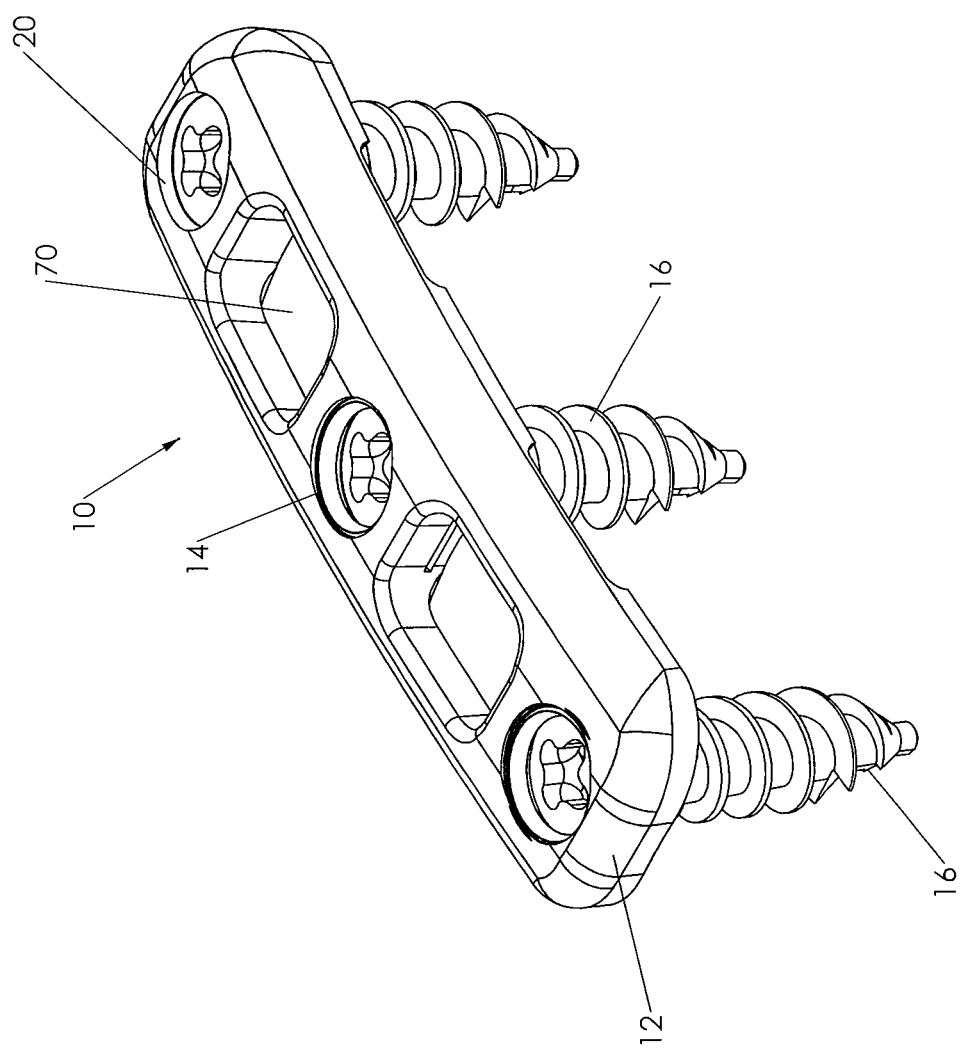
FIG. 1 is a perspective view of the plate, mounting screws and axial retention clips.
Figure 6:
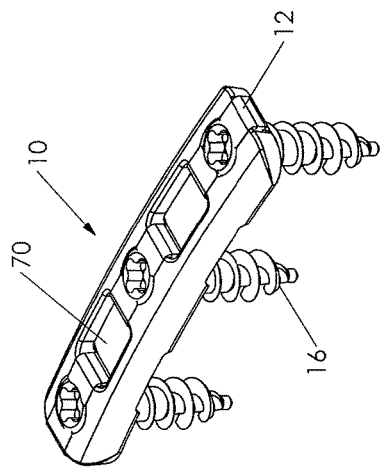
FIG. 6 is a perspective view of the plate, mounting screws and axial retention clip.
Figure 7:
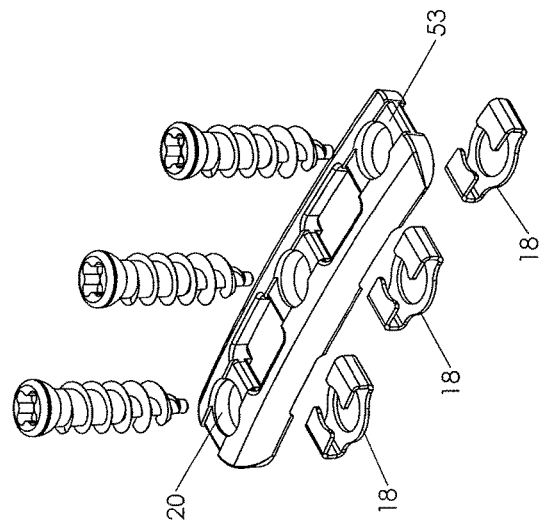
FIG. 7 is an exploded view of FIG. 4.
Figure 2:
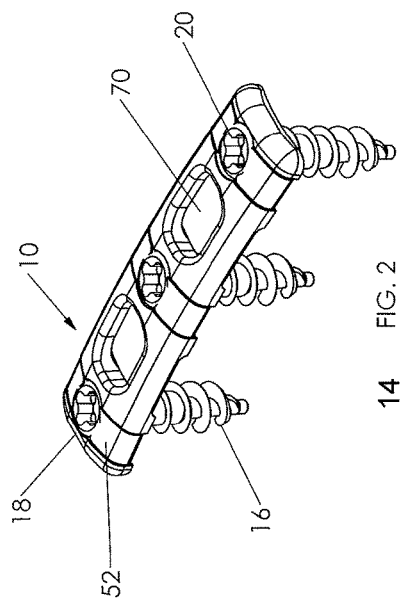
FIG. 2 is a perspective view of the plate, mounting screws and lateral retention clips.
Figure 3:
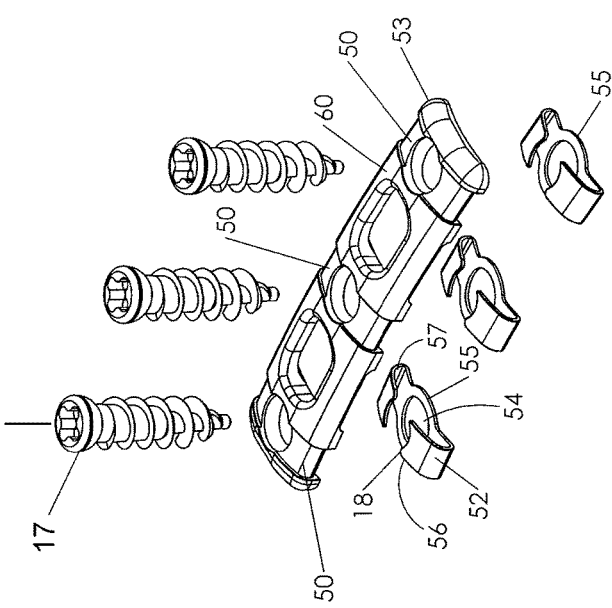
FIG. 3 is an exploded view of FIG. 2.
Figure 5:
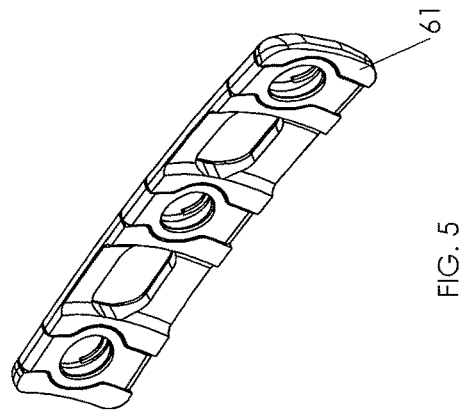
FIG. 5 is a bottom perspective view of the plate with lateral retention clips.
Figure 9:
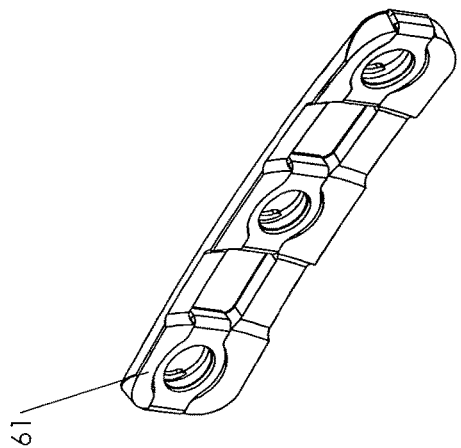
FIG. 9 is a bottom perspective view of the plate with axial retention clips.
Figure 4:
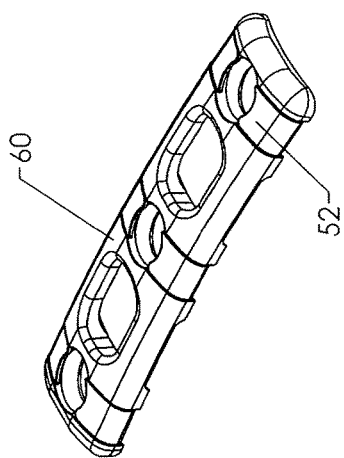
FIG. 4 is a top perspective view of the plate with lateral retention clips.
Figure 8:
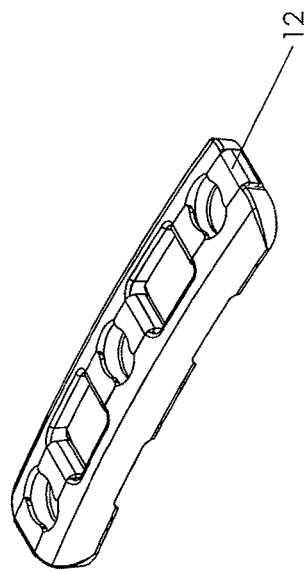
FIG. 8 is a top perspective view of the plate with axial retention clips.

Referring to the Figures, set forth is a cervical plate 10, the cervical plate 10 having improved mounting screws 16 that employ retention clips 12 that engage the plate and fit over the head portion 14 of the mounting screw 16. The screw heads engage an edge 18 of the retention clip 12 during installation allowing ease of insertion wherein the mounting screw 16 pushes aside the edge 18 of the retention clip 12. If the mounting screw 16 is not fully inserted, the retention clip 12 will not engage over the head portion 14 providing a visual indicator of proper mounting screw 16 positioning. The retention clip 12 is constructed to automatically engage the head portion 14 of the mounting screw 16 during insertion of the screw into countersunk apertures 20. The arrangement prevents the mounting screws 16 from migrating out of the bone material during use. The retention clip 12 wraps around the plate, and includes a pass through aperture that can be viewed in the alternative embodiment set forth in FIGS. 1 and 6-9. In some embodiments, the cervical plate comprises visual or physical access ports 70, optionally allowing the surgeon to view the correct positioning of the device and/or to allow for physical access of, for example, surgical or other instruments during the insertion of the cervical plate, if desired.

In some embodiments, the cervical plate 10 comprises improved mounting screws that employ retention clips that engage the plate and fit over the top of the screw, not shown. The screw heads engage an edge of the retention clip during installation allowing ease of insertion wherein the mounting screw pushes aside the edge of the retention clip. The retention clip is constructed to automatically engage the head portion of the screw during insertion into countersunk apertures. The arrangement prevents the mounting screws from migrating out of the bone material during use. Alternatively, the mounting screw 16 may include a groove 17 for engaging the first and second ends of the retention clips and preventing migration of the screws. The retention clip wraps around the plate and includes a pass through aperture. FIGS. 2-5 show the lateral 52 retention clips. The retention clip comprises a central body 55 having an aperture 54 disposed therewith, a first arm 56, a second arm 57, wherein the first and second arms fold over creating opposing ends for wrapping around the plate 53. The plate having grooves or recesses 50 wherein the grooves or recesses are anatomically shaped and dimensioned for receiving the retention clip, the grooves or recesses being disposed on the top surface 60 of the plate or the bottom surface 61 of the plate, or combinations thereof, and positioned laterally 52.

In preferred embodiments, the arms of the retention clip can exhibit a degree of flexibility. The flexibility of the arms allow for the clips to insert the clips onto the cervical plate 10. The degree of flexibility can be varied depending on the materials used to construct the retention clips, physical properties (for example modulus, elastic limit, etc, which might for example be introduced through different processing techniques), dimensions (cross-sectional size (for example diameter when the cross-sectional shape is circular, or width when it is square or rectangular), and cross-sectional shape (for example rounded, or polygonal etc), thickness of the materials, the angle of the fold in the arms of the retention clip, length of the arms and the like. In preferred embodiments, the retention clips comprise: shape memory alloys (e.g. nitinol), shape memory polymers, stainless steel and alloys thereof, titanium, titanium alloys, metallic alloys, polymeric materials, thermoplastics, thermoplastic composites, organic polymer thermoplastics (e.g., polyether ether ketone (PEEK)), plastics, plastic composites, ceramic or combinations thereof. In some embodiments, one or more components, e.g. first and second arms, planar center, of the retention clips can comprise any one or more materials.

If desired, the device components, for example, cervical plate, retention clips, biasing members, mounting screws, can be manufactured from one or more materials and, as such, would differ from one another.

Figure 10:
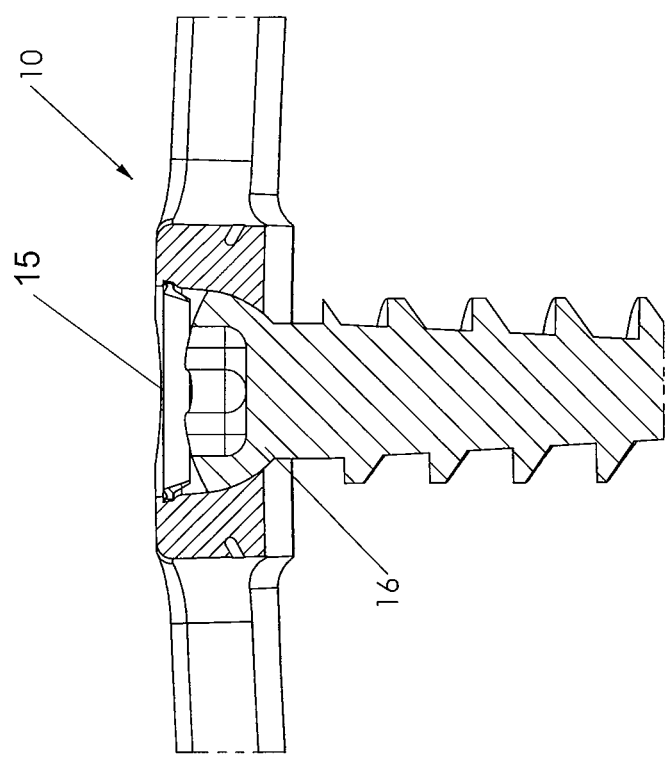
FIG. 10 is a cross sectional view.
Figure 11:
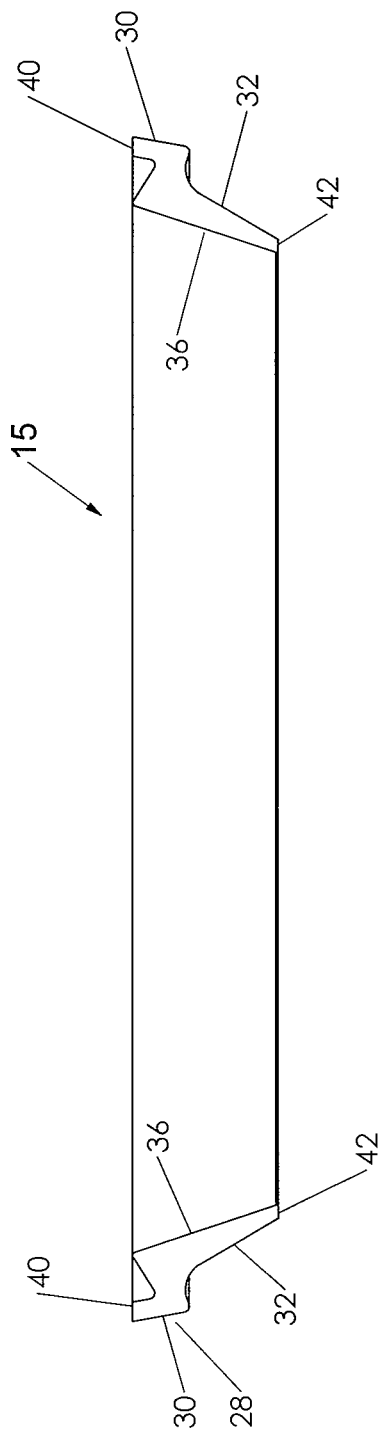
FIG. 11 is a cross sectional view of the spring element.
Figure 12:
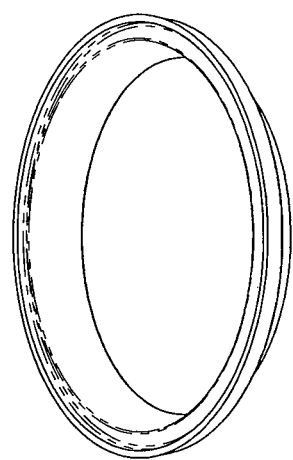
FIG. 12 is a another embodiment of a spring element.
Figure 13:
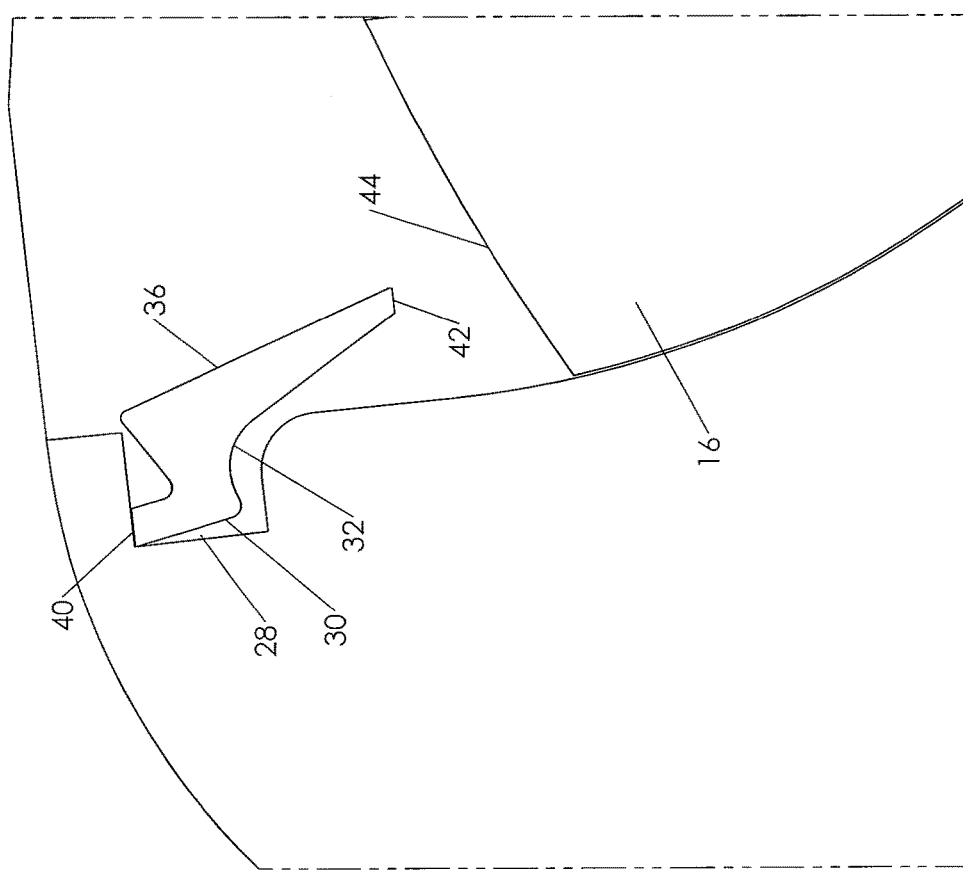
FIG. 13 is an enlarged element view of the spring element.
Figure 14:
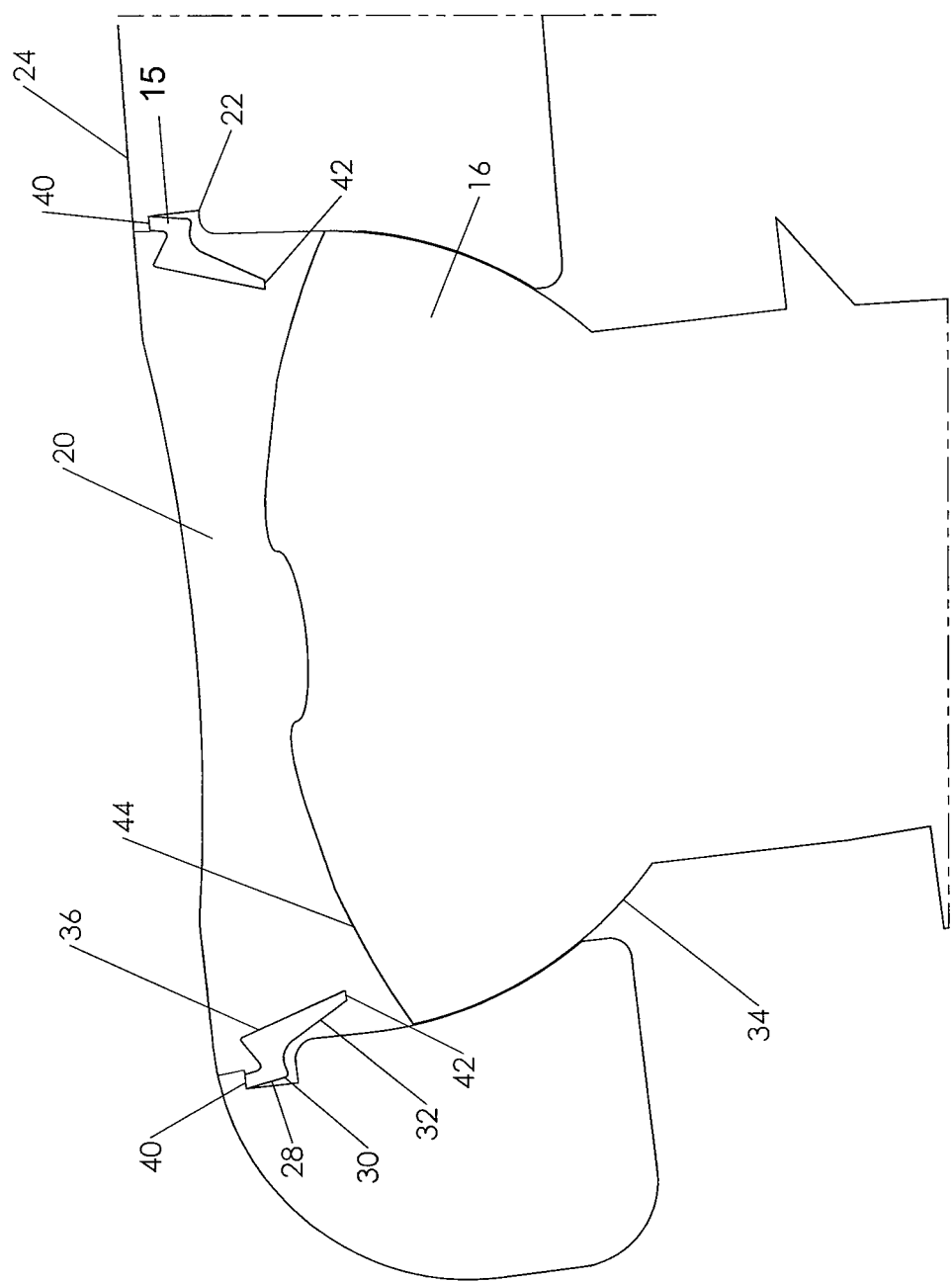
FIG. 14 is an enlarged element view of the spring element.

Set forth in FIG. 10, is a cervical plate 10 having a mounting screw 12 that engages a spring biasing member 15 upon installation of the screw. The mounting screw head 16 engages the biasing member 15 to allow directional rotation of the mounting screw 12 into the mounting screw aperture or hole. During installation, the screw head 16 causes the biasing member to stretch into an open position and allow the screw head 16 to pass. The spring biasing member 15 is preferably made of polyether ether ketone (PEEK) which is an organic polymer thermoplastic. While PEEK is not traditionally a shape memory polymer, a variation of the PEEK material now allows shape memory behavior.

For installation, the plate 10 has a screw mount aperture 20 with a lip recess 22 formed beneath the surface 24 of the plate. The lip recess 22 is placed about the circumference of the screw mount 20 and is constructed and arranged to receive a portion of the spring biasing member 15. The spring biasing member 15 having an outer surface 28 that has a recess engagement portion 30 and a support surface 32. The support surface 32 providing a biasing position to allow entrance of a screw head 16 having a curved entrance surface 34 to pass a tapered inner surface 36 of the biasing member 15.

Once the biasing member 15 has received the screw head 16, the biasing member 15 prevents the screw from migrating out of the bone material during use of the device. The locking mechanism operates simultaneously with the placement of the screws into the screw mounting apertures. A lip 40 of the biasing member will engage the ceiling of the recess and force the biasing member 15 to close by engagement of tip 42 along the screw head surface 44. The biasing members 15 can be removed by a screw driver or the like tool to permit post-operative removal of the implant if necessary.

Figure 15:
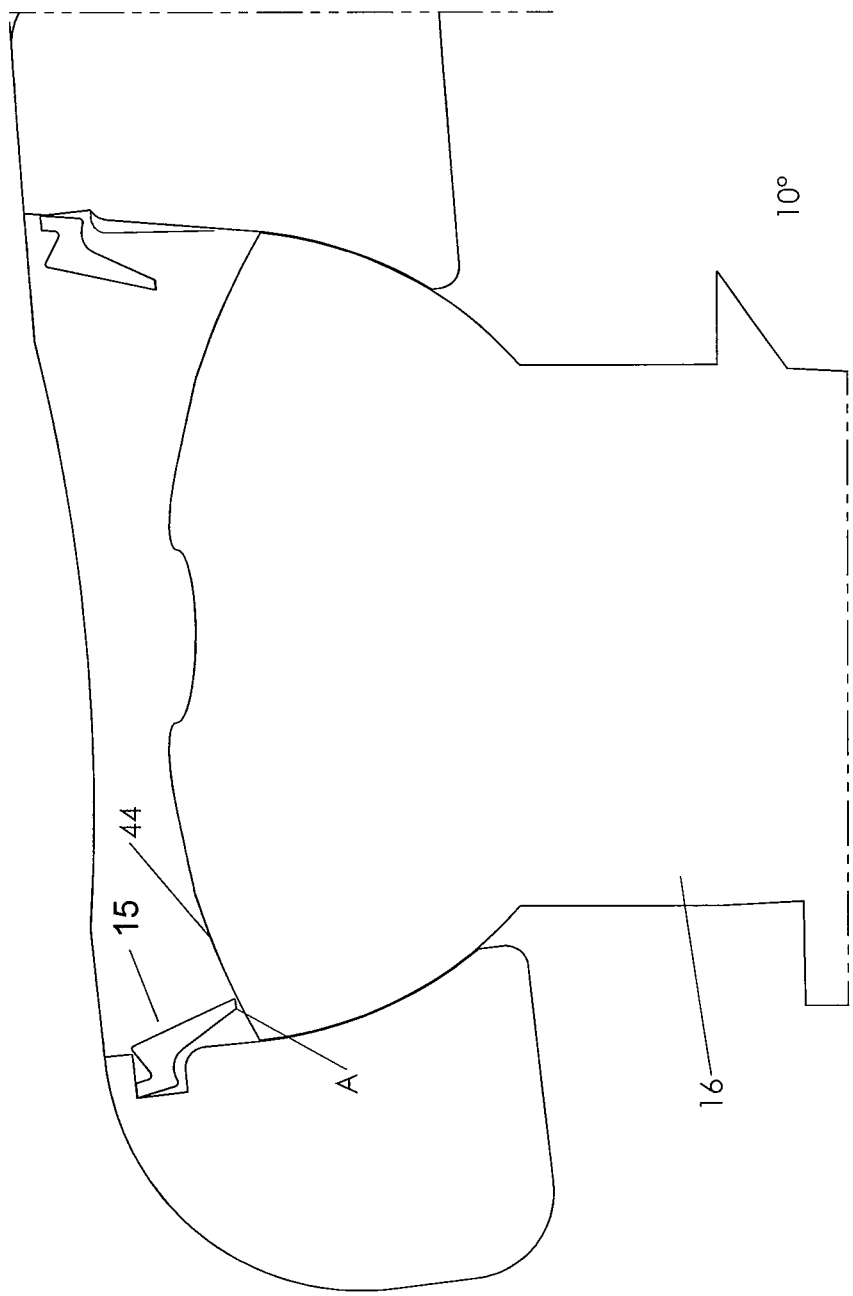
FIG. 15 is a cross sectional view of the screw at a positive 10° position.
Figure 16:
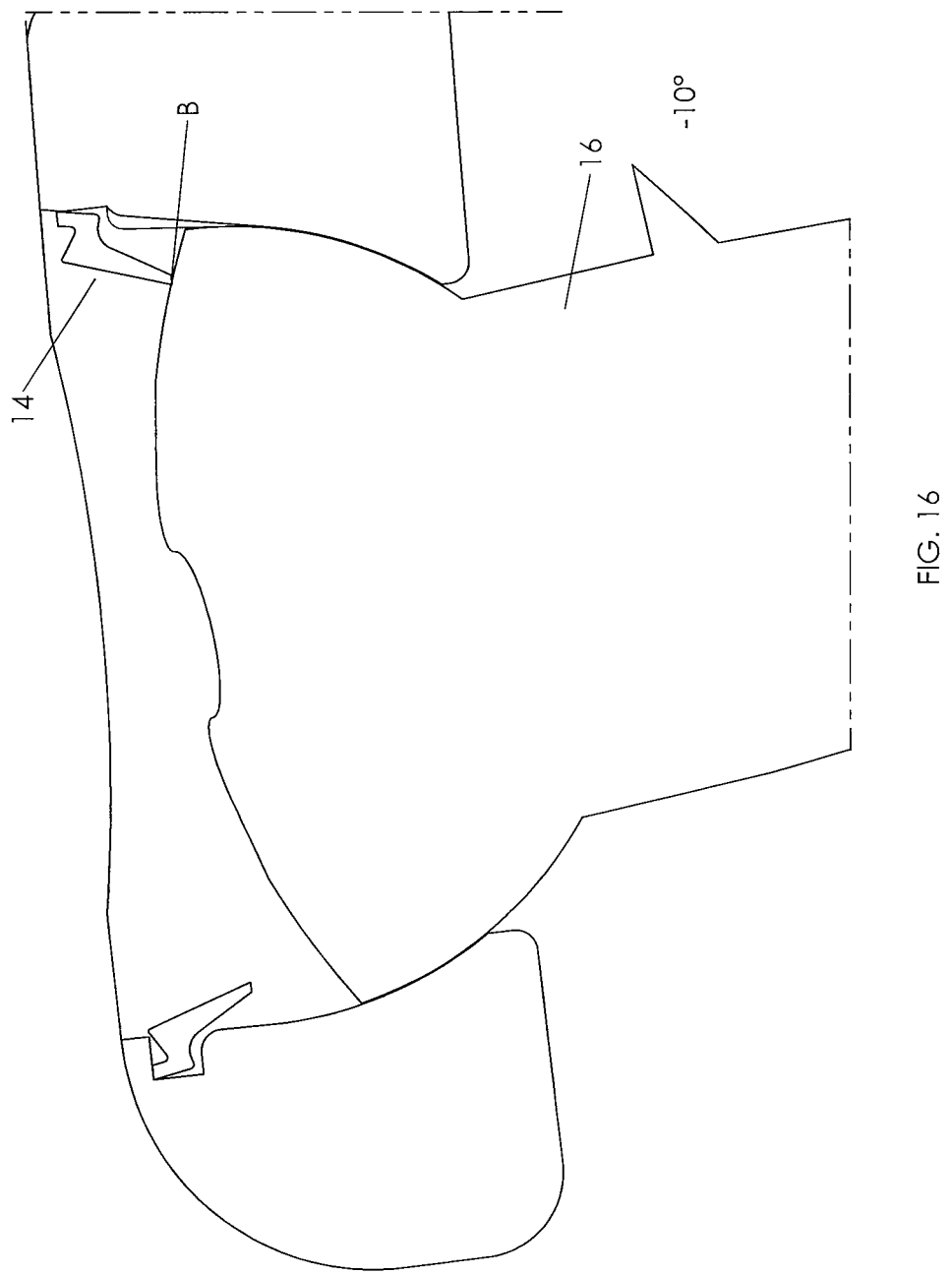
FIG. 16 is a cross sectional view of the screw at a negative 10° position.
Figure 17:
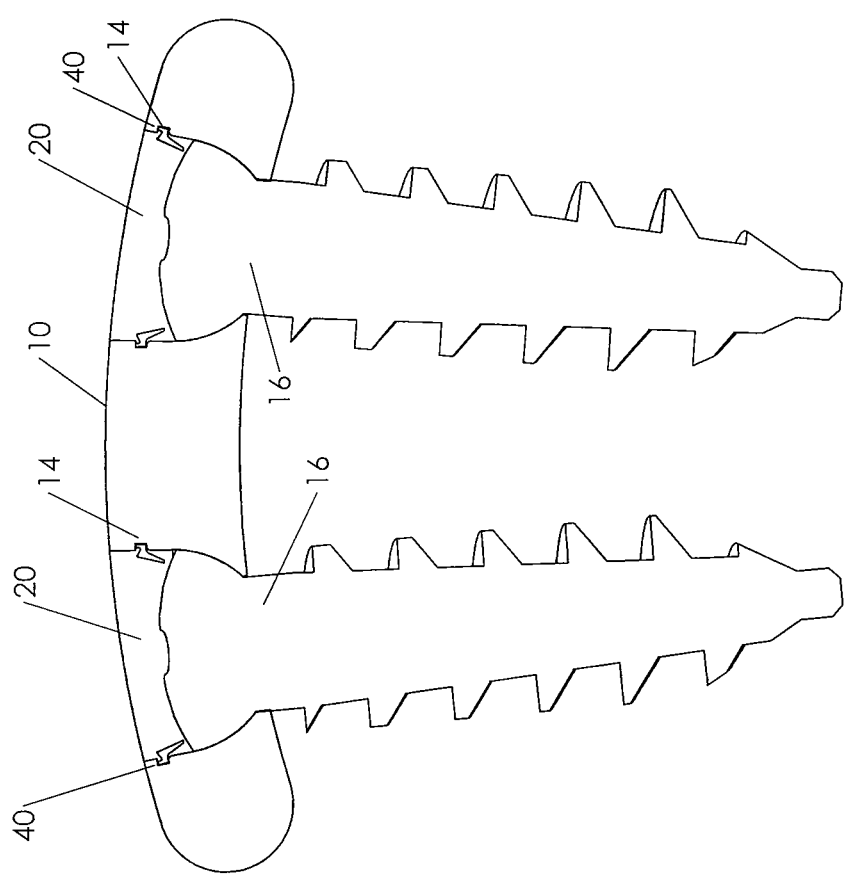
FIG. 17 is a cross sectional view of two screws captured beneath the spring elements.

Referring to FIG. 15, the angular movement of the screw 12 is illustrated by a positive 10 degree angle wherein the screw head surface 44 is angled to a position approaching point A on the biasing member 15. Referring to FIG. 16, the angular movement of the screw 12 is further illustrated by a negative 10 degree angle wherein the screw head surface 44 is angled to a position approaching point B on the biasing member 15.

Having described certain details of the device(s) and components thereof, various embodiments are provided. In one preferred embodiment, a device for immobilizing bones or bone fragments in a preselected spatial orientation comprises a plate, a retention clip, a mounting screw, a screw mount aperture, apertures or combinations thereof. In preferred embodiments, the plate is elongated and comprises a planar surface, a curved surface or combinations thereof.

In another preferred embodiment, the screw mount aperture comprises a lip recess disposed beneath the surface of the plate. In another preferred embodiment, the lip recess is placed about the circumference of the screw mount aperture and is constructed and arranged to receive a portion of a biasing member.

In yet another preferred embodiment, the biasing member comprises an outer surface having a recess engagement portion and a support surface, the support surface having a curved entrance surface and a tapered inner surface providing a biasing position for entrance of a screw head.

In preferred the mounting screw head engages the biasing member allowing for directional rotation of the mounting screw into the mounting screw hole. In another preferred embodiment, the screw head causes the biasing member to stretch into an open position, thereby allowing the mounting screw head to pass.

In another preferred embodiment, the retention clip comprises a central body having an aperture disposed therewith, a first arm, a second arm, wherein the first and second arms fold over creating opposing ends for wrapping around the plate. In preferred embodiments, the retention clips are removable.

In another preferred embodiment, the plate further comprises one or more apertures, ports, grooves or recesses, wherein the grooves or recesses are anatomically shaped and dimensioned for receiving a retention clip, the grooves or recesses being disposed on a top surface of the plate, a bottom surface of the plate, and positioned laterally or axially.

In yet another preferred embodiment, the mounting screws comprise a groove for engaging the first and second ends of the retention clips and preventing migration of the screws.

In yet another preferred embodiment, the retention clips are formed of one or more biocompatible materials comprising: shape memory alloys (e.g. nitinol), shape memory polymers, stainless steel and alloys thereof, titanium, titanium alloys, metallic alloys, polymeric materials, thermoplastics, thermoplastic composites, organic polymer thermoplastics (e.g., polyether ether ketone (PEEK)), plastics, plastic composites, ceramic or combinations thereof.

In yet another preferred embodiment, a device for immobilizing bones or bone fragments in a preselected spatial orientation comprising a plate having a screw mount aperture with a lip recess disposed beneath the plate's surface.

In some preferred embodiments, the lip recess is placed about the circumference of the screw mount and is constructed and arranged to receive a portion of a biasing member, wherein the biasing member comprises an outer surface having a recess engagement portion and a support surface, the support surface having a curved entrance surface and a tapered inner surface providing a biasing position for entrance of screw head.

In preferred embodiments, wherein, upon engaging a screw head, the biasing member prevents the screw from migrating out of bone material during use of the device.

In another preferred embodiment, a device for immobilizing bones or bone fragments in a preselected spatial orientation comprises a plate, a retention clip, a mounting screw, a screw mount aperture or combinations thereof. Preferably, the plate is elongated and comprises a planar surface, a curved surface or combinations thereof.

In preferred embodiments, the plate further comprises one or more apertures, ports, grooves or recesses. In preferred embodiments, the grooves or recesses are anatomically shaped and dimensioned for receiving the retention clip, the grooves or recesses being disposed on a top surface of the plate, a bottom surface of the plate, or combinations thereof, and positioned laterally or axially.

The retention clips are removable and comprise a central body having an aperture disposed therewith, a first arm, a second arm, wherein the first and second arms fold over creating opposing ends for wrapping around the plate.

The mounting screws comprise a groove for engaging the first and second ends of the retention clips and preventing migration of the screws. The retention clips are preferably formed of one or more biocompatible materials comprising shape memory alloys (e.g. nitinol), shape memory polymers, stainless steel and alloys thereof, titanium, titanium alloys, metallic alloys, polymeric materials, thermoplastics, thermoplastic composites, organic polymer thermoplastics (e.g., polyether ether ketone (PEEK)), plastics, plastic composites, ceramic or combinations thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the term "shape memory" is a property of select materials that have the ability to "remember" the shape given during original thermo-mechanical processing allowing the material to revert to that original shape when subjected to heat. For example, nickel titanium, or "Nitinol", properties include the shape memory effect, superelasticity, and high damping capability.

As used herein, "shape-memory polymers" (SMPs) are polymeric smart materials that have the ability to return from a deformed state (temporary shape) to their original (permanent) shape induced by an external stimulus (trigger), such as temperature change.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A cervical plate comprising:
   a plate having a first end wall and a second end wall defining a length therebetween with an upper surface separated from a lower surface by a first sidewall and second sidewall;
   at least two screw mount apertures positioned in said upper surface of said plate and separated by an access port extending from said upper surface to lower surface;
   a mounting screw having a threaded shank and a screw head constructed and arranged to fit interface with each said screw mount aperture, wherein each said screw mount aperture is sized to pass the threaded shank of said mounting screw and retain said screw head from passing through said upper surface of said plate;
   a recessed groove placed around each said screw mount aperture, said recessed groove extending from said upper surface of said plate to said lower surface of said plate;
   a removable retention clip constructed and arranged for placement with said recessed groove for securement around each said screw mount aperture, said retention clip having a flexible body with a centrally disposed aperture positional along said lower surface of said plate with first and second arms that extend from said lower surface to said upper surface wherein first and second ends of said retention clip form opposing ends which are juxtapositioned to said screw mount aperture along the upper surface of said plate;
   whereby said opposing ends of said retention clip are available for engaging said mounting screw head wherein the opposing ends of the retention clip inhabit the removal of an installed mounting screw.

2. The cervical plate according to claim 1, wherein the screw head causes the opposing ends of the retention clip to flex into an open position thereby allowing the mounting screw head to pass.

3. The cervical plate according to claim 1, wherein each said recessed groove is anatomically shaped and dimensioned for receiving said retention clip, each said groove positioned laterally or axially.

4. The cervical plate according to claim 1, wherein the screw head of said mounting screw includes a groove for engaging the first and second ends of the retention clips.

5. The cervical plate according to claim 1, wherein said retention clips and plate are formed of one or more biocompatible materials from the group comprising of: shape memory alloys, shape memory polymers, nitinol, stainless steel and alloys thereof, titanium, titanium alloys, metallic alloys, polymeric materials, thermoplastics, thermoplastic composites, organic polymer thermoplastics, plastics, polyether ether ketone (PEEK), plastic composites, ceramic or combinations thereof.

6. The cervical plate according to claim 1 wherein said retention clip is mounted axially and extends around an end wall of said plate and an edge of an access port.

7. The cervical plate according to claim 1 wherein said retention clip is mounted laterally and extends around each sidewall of said plate.

* * * * *